US006646138B2

(12) United States Patent
Oku et al.

(10) Patent No.: US 6,646,138 B2
(45) Date of Patent: Nov. 11, 2003

(54) PROCESS FOR PRODUCING PROPYLENE OXIDE

(75) Inventors: Noriaki Oku, Chiba (JP); Tateo Seo, Chiba (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/042,136

(22) Filed: Jan. 11, 2002

(65) Prior Publication Data

US 2002/0151730 A1 Oct. 17, 2002

Related U.S. Application Data

(63) Continuation-in-part of application No. PCT/JP00/04611, filed on Jul. 10, 2000.

(51) Int. Cl.$^7$ .............................................. C07D 301/19
(52) U.S. Cl. ...................................... 549/529; 549/541
(58) Field of Search .................................. 549/529, 541

(56) References Cited

U.S. PATENT DOCUMENTS

| 3,350,422 A | 10/1967 | Kollar |
| 5,374,747 A | 12/1994 | Saxton et al. |
| 5,453,511 A | 9/1995 | Saxton |
| 5,527,520 A | 6/1996 | Saxton et al. |
| 5,695,736 A | 12/1997 | Saxton et al. |
| 5,723,637 A | 3/1998 | Tsuji et al. |

FOREIGN PATENT DOCUMENTS

| EP | 0 659 685 A1 | 6/1995 |
| GB | 1130231 | 10/1968 |
| JP | 2000-107604 A | 4/2000 |
| JP | 2000-107605 A | 4/2000 |
| JP | 2000-109469 A | 4/2000 |
| JP | 2000-109470 A | 4/2000 |

*Primary Examiner*—Ba K. Trinh
(74) *Attorney, Agent, or Firm*—Sughrue Mion, PLLC

(57) ABSTRACT

A process for producing propylene oxide comprising the following steps:

oxidation step: a step of obtaining isopropylbenzene hydroperoxide by oxidizing isopropylbenzene;

epoxidation step: a step of obtaining propylene oxide and cumyl alcohol by reacting propylene with isopropylbenzene hydroperoxide obtained in the oxidation step;

hydrogenolysis step: a step of obtaining isopropylbenzene by hydrogenolyzing cumyl alcohol obtained in the epoxidation step, and recycling this isopropylbenzene to the oxidation step as a raw material of the oxidation step; and organic acid removal step: a step of removing an organic acid out of the system in at least one point in said steps or between said steps.

9 Claims, No Drawings

PROCESS FOR PRODUCING PROPYLENE OXIDE

This is a Continuation-in-Part of PCT application No. PCT/JP00/04611 filed on Jul. 10, 2000.

BACKGROUND OF THE INVENTION

1. Technical Field

The present invention relates to a process for producing propylene oxide. More particularly, the present invention relates to a process for producing propylene oxide in which propylene is converted into propylene oxide in high yield using a hydroperoxide of isopropylbenzene as an oxygen carrier and said isopropylbenzene can be recycled.

2. Background Art

A process for oxidizing propylene by using a hydroperoxide of ethylbenzene as an oxygen carrier to obtain propylene oxide and styrene is known as a Halcon process. This process, however, is unsatisfactory from the standpoint of selective production of only propylene oxide in high yield, since styrene is by-produced together with propylene oxide.

SUMMARY OF THE INVENTION

The present inventors have intensively studied a process for producing propylene oxide not having the above-mentioned problem, resultantly found that propylene can be converted into propylene oxide without production of by-products by using a hydroperoxide of isopropylbenzene as an oxygen carrier and propylene oxide can be obtained at high yield by adding a process for removing an organic acid, and thus completed the present invention.

Namely, the present invention relates to a process for producing propylene oxide comprising the following steps:

oxidation step: a step of obtaining isopropylbenzene hydroperoxide by oxidizing isopropylbenzene;

epoxidation step: a step of obtaining propylene oxide and cumyl alcohol by reacting propylene with isopropylbenzene hydroperoxide obtained in the oxidation step;

hydrogenolysis step: a step of obtaining isopropylbenzene by hydrogenolyzing cumyl alcohol obtained in the epoxidation step, and recycling this isopropylbenzene to the oxidation step as a raw material of the oxidation step; and organic acid removal step: a step of removing an organic acid out of the system in at least one point in said steps or between said steps.

DETAILED DESCRIPTION OF THE INVENTION

The oxidation step in the present invention is a step for obtaining isopropylbenzene hydroperoxide by oxidizing isopropylbenzene. The oxidation of isopropylbenzene is usually conducted by auto-oxidation using an oxygen-containing gas such as air, oxygen-concentrated air or the like. Particularly, an emulsion oxidation method in an alkaline aqueous emulsion is preferable from the standpoint of improving the yield of isopropylbenzene hydroperoxide. The usual reaction temperature is from 50 to 200° C., and the reaction pressure is usually from atmospheric pressure to 5 MPa. In the emulsion oxidation method, an alkali metal compound such as NaOH or KOH, alkaline earth metal compound, or alkali metal carbonate such as $Na_2CO_3$ or $NaHCO_3$, $NH_3$, $(NH_4)_2CO_3$, alkali metal ammonium carbonates or the like is used as an alkaline reagent.

The epoxidation step in the present invention is a step of reacting an organic hydroperoxide obtained in the oxidation step with propylene to obtain propylene oxide and cumyl alcohol. The epoxidation step is preferably carried out in the presence of a catalyst comprising a titanium-containing silicon oxide from the viewpoint of obtaining the object matter under high yield and high selectivity. As these catalysts, so-called Ti-silica catalysts containing Ti chemically bonded to silicon oxide are preferable. For example, a compound prepared by supporting a Ti compound on a silica carrier, a compound prepared by combining a Ti compound with silicon oxide by a coprecipitation method or sol gel method, zeolite compounds containing Ti, and the like are listed.

It is preferable that such a titanium-containing silicon oxide satisfies all of the following conditions (1) to (3).

The condition (1) is that an average pore diameter is 10 Å or more.

The condition (2) is that pores in 90% or more of volume of all pores, have a pore diameter of from 5 to 200 Å.

The condition (3) is that a specific pore volume is 0.2 $cm^3/g$ or more.

Here, the above-mentioned specific pore volume means a pore volume per g of a catalyst.

The measurements in the above-mentioned conditions (1) to (3) can be conducted by ordinary methods using a physical adsorption method for a gas such as nitrogen, argon or the like.

It is preferable that the titanium-containing silicon oxide satisfies the following condition (4) in addition to the above-mentioned conditions (1) to (3).

The condition (4) is that a titanium-containing silicon oxide is obtained by using a quaternary ammonium ion of the following general formula (I) as a template and then removing the template.

$$[NR^1R^2R^3R^4]^+ \qquad (1)$$

(wherein, $R^1$ represents a linear or branched hydrocarbon group having 2 to 36 carbon atoms, and $R^2$ to $R^4$ represent an alkyl group having 1 to 6 carbon atoms.).

$R^1$ is a linear or branched hydrocarbon group having 2 to 36 carbon atoms, preferably having 10 to 18 carbon atoms. $R^2$ to $R^4$ are an alkyl group having 1 to 6 carbon atoms, and it is preferable that all of $R^2$ to $R^4$ are a methyl group. As the specific examples of the quaternary ammonium ion of the general formula (I), cations such as hexadecyltrimethylammonium, dodecyltrimethylammonium, benzyltrimethylammonium, dimethyldidodecylammonium, hexadecylpyridinium and the like can be listed.

As the method for removing a template, removal by a calcination, removal by an extraction, and the like are listed, and the extraction is preferable for maintaining activity and selectivity of a catalyst at high level. It is preferable that the catalyst has an absorption peak in the region of 960±5 $cm^{-1}$ in the infrared absorption spectrum. This peak is supposed to correspond to titanium introduced in a silica skeleton. A catalyst can be used in any physical forms such as a powder, flake, spherical particle and pellet. As the specific and preferable methods for obtaining a catalyst, the following methods can be listed.

First, a silica source, a titanium source and a quaternary ammonium ion as a template are mixed and stirred in liquid condition to obtain a solid containing the catalyst components and template. When a reagent used is in the form of solid, it is advantageous to dissolve or disperse the reagent in a solvent to give a solution to be used.

As the silica source, amorphous silica and alkoxysilanes, for example, tetramethyl orthosilicate, tetraethyl orthosilicate, tetrapropyl orthosilicate and the like are listed.

As the titanium source, titanium alkoxides, for example, tetramethyl titanate, tetraethyl titanate, tetrapropyl titanate, tetraisopropyl titanate, tetrabutyl titanate, tetraisobutyl titanate, tetra-2-ethylhexyl titanate, tetraoctadecyl titanate, and titanium (IV) oxyacetylacetonate, titanium (IV) diisopropoxy bisacetylacetonate and the like, or halogenated titaniums, for example, titanium tetrachloride, titanium tetrabromide, titanium tetraiodide and the like, are listed.

As the template, those described above can be used.

As the examples of the solvent, water and alcohols, for example, methanol, ethanol, n-propanol, 2-propanol, n-butanol, sec-butanol, t-butanol, vinyl alcohol, allyl alcohol, cyclohexanol, benzyl alcohol and the like, diols, or mixtures thereof, and the like are listed.

The molar ratio of the use amount of a titanium source to the use amount of a silica source is preferably from $10^{-5}$ to 1, more preferably from 0.00008 to 0.4. The molar ratio of the use amount of a quaternary ammonium ion to the total amount of a silica source and a titanium source is preferably from $10^{-2}$ to 2.

For promoting the reaction of a silica source and a titanium source, it is preferable to impart alkaline or acidic property to a mixed solution. As the alkali source, quaternary ammonium hydroxides are preferable, and examples thereof include tetramethyl ammonium hydroxide, tetraethyl ammonium hydroxide, tetrapropyl ammonium hydroxide and the like. As examples of the acid, inorganic acids such as hydrochloric acid, sulfuric acid, nitric acid and the like, and organic acids such as formic acid, acetic acid, propionic acid and the like are listed.

The mixing and stirring temperature is usually from –30 to 100° C. A solid is formed by mixing and stirring, and this may also be aged for further growth of the solid. The aging time is usually 180 hours or less, and the aging temperature is usually from 0 to 200° C. When heating is required in aging, it is preferable to transfer the mixture into a pressure-resistant vessel and aging of the mixture is conducted air-tightly for avoiding vaporization of the solvent.

Next, the solid obtained in the above-mentioned step is subjected to a solvent extraction operation using a solvent to remove a template, thereby obtaining an intended catalyst. A technology for extracting out a template by a solvent is reported, for example, by Whitehurst et al. (see, U.S. Pat. No. 5,143,879).

The solvent used for extraction may advantageously be that which can dissolve a compound used as a template, and generally, oxa- and/or oxo-substituted hydrocarbons having 1 to about 12 carbon atoms which are liquid at normal temperature can be used. As the suitable solvent of this kind, alcohols, ketones, ethers (acyclic and cyclic) and esters can be used, and examples thereof include hydroxy-substituted hydrocarbons such as methanol, ethanol, ethylene glycol, propylene glycol, isopropanol, n-butanol and octanol; oxo-substituted hydrocarbons such as acetone, diethyl ketone, methyl ethyl ketone and methyl isobutyl ketone; hydrocarbon ethers such as diisobutyl ether and tetrahydrofuran; hydrocarbon esters such as methyl acetate, ethyl acetate, butyl acetate and butyl propionate; and the like. The weight ratio of these solvents to a catalyst is usually from 1 to 1000, preferably from 10 to 300. For improving extraction effect, acids or salts thereof may be added to these solvents. Examples of acids used include inorganic acids such as hydrochloric acid, sulfuric acid, nitric acid, hydrobromic acid and the like, and organic acids such as formic acid, acetic acid, propionic acid and the like. Examples of salts thereof include alkali metal salts, alkaline earth metal salts, ammonium salts and the like. The concentration of an acid or salt thereof added in a solvent is preferably 10 mol/l or less, further preferably 1 mol/l or less. When the concentration of an acid or salt thereof added in a solvent is too large, titanium present in a catalyst is eluted, leading to decrease in catalytic activity in some cases. After sufficient mixing of a solvent and a catalyst, a liquid phase part is separated by filtration, decantation or the like. This operation is repeated for required times. Extraction can also be conducted by flowing a washing solvent through a catalyst layer. Completion of washing can be known, for example, by analysis of a liquid phase part. The extraction temperature is preferably from 0 to 200° C., further preferably from 20 to 100° C. Instead of use of the above-mentioned organic extraction solvent, extraction can also be conducted by using supercritical fluid. As the supercritical fluid, carbon dioxide is preferable. The supercritical temperature of carbon dioxide is about 31° C. or more, and the extraction temperature is preferably from 31 to 100° C., further preferably from 35 to 60° C. The supercritical pressure is about 7.4 MPa, and preferably from 10 to 30 MPa. It is preferable to conduct extraction, using supercritical carbon dioxide in an amount of 50 to 500 g per minute per liter of a catalyst in extraction, for a period of 4 to 20 hours.

A drying may be performed on a solid obtained after the extraction. Namely, the solid is heated, under an atmosphere of a non-reducing gas, for example, nitrogen, argon or carbon dioxide, or an oxygen-containing gas, for example, air, at a temperature preferably from 10 to 800° C., further preferably from 50 to 300° C.

A silylation is preferably performed on thus obtained catalyst. The silylation is conducted by contacting the resulted catalyst with a silylating agent to convert a hydroxyl group present on the surface of the catalyst into a silyl group. Examples of the silylating agent include organic silanes, organic silylamines, organic silylamides and derivatives thereof, and organic silazanes and other silylating agents.

Examples of the organic silane include chlorotrimethylsilane, dichlorodimethylsilane, chlorobromodimethylsilane, nitrotrimethylsilane, chlorotriethylsilane, iododimethylbutylsilane, chlorodimethylphenylsilane, dichlorodimethylsilane, dimethyl n-propylchlorosilane, dimethylisopropylchlorosilane, t-butyldimethylchlorosilane, tripropylchlorosilane, dimethyloctylchlorosilane, tributylchlorosilane, trihexylchlorosilane, dimethylethylchlorosilane, dimethyloctadecylchlorosilane, n-butyldimethylchlorosilane, bromomethyldimethylchlorosilane, chloromethyldimethylchlorosilane, 3-chloropropyldimethylchlorosilane, dimethoxymethylchlorosilane, dimethylphenylchlorosilane, triethoxychlorosilane, dimethylphenylchlorosilane, methylphenylvinylchlorosilane, benzyldimethylchlorosilane, diphenyldichlorosilane, diphenylmethylchlorosilane, diphenylvinylchlorosilane, tribenzylchlorosilane and 3-cyanopropyldimethylchlorosilane.

Examples of the organic silylamine include N-trimethylsilylimidazole, N-t-butyldimethylsilylimidazole, N-dimethylethylsilylimidazole, N-dimethyl n-propylsilylimidazole, N-dimethylisopropylsilylimidazole, N-trimethylsilyldimethylamine, N-trimethylsilyldiethylamine, N-trimethylsilylpyrrole, N-trimethylsilylpyrrolidine, N-trimethylsilylpiperidine, 1-cyanoethyl(diethylamino)dimethylsilane and pentafluorophenyldimethylsilylamine.

Examples of the organic silylamide and derivative thereof include N,0-bistrimethylsilylacetamide, N,0-bistrimethylsilyltrifluoroacetamide, N-trimethylsilylacetamide, N-methyl-N-trimethylsilylacetamide, N-methyl-N-trimethylsilyltrifluoroacetamide, N-methyl-N-trimethylsilylheptafluorobutylamide, N-(t-butyldimethylsilyl)-N-trifluoroacetamide and N,0-bis(diethylhydrosilyl)trifluoroacetamide.

Examples of the organic silazane include hexamethyldisilazane, heptamethyldisilazane, 1,1,3,3-tetramethyldisilazane, 1,3-bis(chloromethyl)tetramethyldisilazane, 1,3-divinyl-1,1,3,3-tetramethyldisilazane and 1,3-diphenyltetramethyldisilazane.

Disclosed as examples of other silylating agents are N-methoxy-N,0-bistrimethylsilyltrifluoroacetamide, N-methoxy-N,0-bistrimethylsilyl carbamate, N,0-bistrimethylsilyl sulfamate, trimethylsilyltrifluoromethane sulfonate and N,N'-bistrimethylsilylurea. The preferable silylating agent is hexamethyldisilazane.

Thus prepared catalyst has high surface area and highly dispersed titanium active sites, and can be suitably used in an olefin epoxidation reaction.

In the present invention, isopropylbenzene hydroperoxide used as a raw material for the epoxidation process may be a dilute or dense purified substance or non-purified substance.

The epoxidation reaction is conducted by contacting propylene and isopropylbenzene hydroperoxide with a catalyst. The reaction can be carried out in liquid phase using a solvent. The solvent must be liquid under temperature and pressure in the reaction, and substantially inert to reactants and products. The solvent may be that which is composed of a substance present in a hydroperoxide solution used. For example, when isopropylbenzene hydroperoxide is a mixture with isopropylbenzene which is a raw material thereof, this can be used instead of a solvent without particularly adding a solvent. Additionally, monocyclic aromatic compounds (e.g. benzene, toluene, chlorobenzene, orthodichlorobenzene), and alkanes (e.g. octane, decane, dodecane) and the like are listed as useful solvents.

The epoxidation temperature is usually from 0 to 200° C., and preferably from 25 to 200° C. The pressuremay be at a level sufficient to keep the reaction mixture in liquid condition. In general, the pressure is advantageously from 100 to 10000 kPa.

The epoxidation reaction can be carried out advantageously using a catalyst in the form of slurry or fixed bed. In the case of a large scale industrial operation, a fixed bed is preferably used. The epoxidation reaction can be conducted by a atch-wise method, semi-continuous method, continuous method or the like. When liquid containing reaction raw materials is passed through a fixed bed, a liquid-like mixture discharged from a reaction region does not contain a catalyst at all or contains substantially no catalyst.

In the present invention, the concentration of an organic acid in oxidation liquid fed to an epoxidation step is preferably 0.5% by weight or less, further preferably 0.1% by weight or less. When the concentration of an organic acid is too high, catalytic activity decreases, and further, catalyst life may be shortened in some cases. The oxidation liquid fed to the epoxidation step includes also reaction liquid produced in this oxidation step, or liquid concentrated by distillation or the like. The organic acid is that having a carboxyl group, and there are exemplified carboxylic acids such as formic acid, acetic acid, propionic acid, benzoic acid and the like, dicarboxylic acids such as oxalic acid, malonic acid, hydroxy acids such as lactic acid, and the like.

The hydrogenolysis step of the present invention is a step in which cumyl alcohol obtained in the epoxidation step is hydrogenolyzed to obtain isopropylbenzene and isopropylbenzene is recycled to an oxidation step as a raw material of an oxidation step. Namely, by hydrogenolysis, that which is the same as isopropylbenzene used in the oxidation step is recycled. The hydrogenolysis reaction is usually conducted by contacting cumyl alcohol and hydrogen with a catalyst. The reaction can be carried out in liquid phase using a solvent or gas phase. The solvent must be substantially inert to reactants and products. The solvent may be that which is composed of a substance present in a cumyl alcohol solution used. For example, when cumyl alcohol is a mixture with isopropylbenzene which is a product, this can be used instead of a solvent without particularly adding a solvent. Additionally, alkanes (e.g., octane, decane, dodecane), monocyclic aromatic compounds (e.g., benzene, ethylbenzene, toluene) and the like are listed as useful solvents. The hydrogenolysis temperature is generally from 0 to 500° C., and preferably from 30 to 400° C. In general, the pressure is advantageously from 100 to 10000 kPa. The hydrogenolysis reaction can be advantageously conducted using a catalyst in the form of slurry or fixed bed. The method of the present invention can be conducted by a batch-wise method, semi-continuous method or continuous method. When liquid or gas containing reaction raw materials is passed through a fixed bed, a liquid-like mixture discharged from a reaction region does not contain a catalyst at all or contains substantially no catalyst.

The organic acid removal step in the present invention is a step of removing an organic acid out of the system at least in each of the oxidation step, epoxidation step and hydrogenolysis step, or at least at one point between these steps. The organic acid removal step may be effected in any point of each step, however, it is preferable to conduct the organic acid removal step between the oxidation step and the epoxidation step from the standpoint of controlling the concentration of an organic acid in oxidation liquid fed to the epoxidation step, within the above-mentioned range. The organic acid removal step can be carried out usually by distillation, extraction or the like. For example, when extraction is used, extraction can be conducted using water or alkaline aqueous solution as an extractant. When an alkaline aqueous solution is used as an extractant, an organic acid can be removed by contacting with an alkaline aqueous solution containing an alkali in amount not less than the molar number of an organic acid fed, leaving the solution, then, removing aqueous phase out of the system. Further, it is preferable to water-wash an oil layer after alkali washing, for removing a remaining alkali and a salt of an organic acid with an alkali. As the alkali, alkali metal compounds such as NaOH and KOH, alkaline earth metal compounds, or alkali metal carbonates such as $Na_2CO_3$ and $NaHCO_3$, or $NH_3$ and $(NH_4)_2CO_3$, alkali metal ammonium carbonates, and the like are used. The organic acid is as described in the column of the epoxidation step.

EXAMPLES

Example 1

Oxidation Step

Cumene is mixed with air, and they are reacted under conditions of a pressure of 300 kPa and a temperature of 150° C. for 5 hours. The oxidation liquid which is formed has the following composition.

Oxidation Liquid Composition

| Cumene hydroperoxide | 35 wt % |
|---|---|
| Cumyl alcohol | 2 wt % |
| Isopropylbenzene | 60 wt % |
| Organic acid | 1.0 wt % |

Organic Acid Removal Step

The oxidation liquid which is obtained in the oxidation step is mixed with a sodium hydroxide aqueous solution at a ratio of the oxidation liquid to the sodium hydroxide aqueous solution of 5:1 for 15 minutes, the mixture is allowed to stand still for 15 minutes, then, an oil layer which is obtained is mixed with water at a ratio of oil layer to water of 5:1 for 15 minutes, and the mixture is allowed to stand still for 15 minutes. An oil layer which is obtained has the following composition.

| Cumene hydroperoxide | 35 wt % |
|---|---|
| Cumyl alcohol | 2 wt % |
| Isopropylbenzene | 60 wt % |
| Organic acid | 0.006 wt % |

The total organic acid concentration in the washed oxidation liquid which is obtained reduces to 0.1 wt % or less by this step.

Epoxidation Step

The washed oxidation liquid which is obtained in the organic acid removal step is allowed to pass continuously through a fixed bed flow reaction vessel in the presence of a Ti-containing silicon oxide catalyst, together with propylene in an amount of 10 foldmol based on 1 mol of isopropylbenzene hydroperoxide in the washed oxidation liquid. The cumene hydroperoxide conversion is kept at 99% by controlling the inlet temperature. The reaction temperature is 60° C. at the time, and the selectivity based on the converted cumene hydroperoxide is 95%.

Comparative Example 1

An epoxidation reaction is conducted under the same conditions as in Example 1 except that organic acid removal is not carried out. The reaction temperature must be elevated to 90° C. At this time, the propylene oxide selectivity becomes 90%. As compared with Example 1, the catalytic activity decreases and propylene oxide yield also decreases.

As described above, the present invention provides a process for producing propylene oxide in which propylene oxide can be obtained in high yield by converting propylene into propylene oxide without producing a by-product using a hydroperoxide of isopropylbenzene as an oxygen carrier and by adding a step of removing an organic acid.

What is claimed is:

1. A process for producing propylene oxide comprising the following steps:

oxidation step: a step of obtaining isopropylbenzene hydroperoxide by oxidizing isopropylbenzene;

epoxidation step: a step of obtaining propylene oxide and cumyl alcohol by reacting propylene with isopropylbenzene hydroperoxide obtained in the oxidation step;

hydrogenolysis step: a step of obtaining isopropylbenzene by hydrogenolyzing cumyl alcohol obtained in the epoxidation step, and recycling this isopropylbenzene to the oxidation step as a raw material of the oxidation step; and organic acid removal step: a step of removing an organic acid out of the system in at least one point in said steps or between said steps.

2. The process according to claim 1, wherein the catalyst used in the epoxidation step is a titanium-containing silicon oxide catalyst.

3. The process according to claim 2, wherein the titanium-containing silicon oxide catalyst satisfies all of the following conditions (1) to (3):

(1) an average pore diameter is 10 Å or more, (2) pores in 90% or more of volume of all pores, have a pore diameter of from 5 to 200 Å, and (3) a specific pore volume is 0.2 cm$^3$/g or more.

4. The process according to claim 2, wherein the titanium-containing silicon oxide catalyst is obtained by using a quaternary ammonium ion of the following general formula (I) as a template and then removing the template:

$$[NR^1R^2R^3R^4]^+ \qquad (I)$$

(wherein, $R^1$ represents a linear or branched hydrocarbon group having 2 to 36 carbon atoms, and $R^2$ to $R^4$ represent an alkyl group having 1 to 6 carbon atoms).

5. The process according to claim 4, wherein the template is removed by an extraction operation.

6. The process according to claim 4, wherein the catalyst has an absorption peak in a region of 960±5 cm$^{-1}$ in the infrared absorption spectrum.

7. The process according to claim 1, wherein the concentration of an organic acid in oxidation liquid fed to an epoxidation step is 0.5% by weight or less.

8. The process according to claim 1, wherein the organic acid removal step is between the oxidation step and the epoxidation step.

9. The process according to claim 7, wherein the concentration of the organic acid is 0.1% by weight or less.